United States Patent [19]

Bugelski et al.

[11] Patent Number: 5,395,848
[45] Date of Patent: Mar. 7, 1995

[54] METHODS OF TREATING HYPERLIPIDEMIA WITH SUBSTITUTED AZASPIRANES

[75] Inventors: Peter J. Bugelski, Philadelphia; Wiliam D. Kerns, West Chester, both of Pa.

[73] Assignee: SmithKline Beecham Corporation, Philadelphia, Pa.

[21] Appl. No.: 211,879

[22] PCT Filed: Oct. 15, 1992

[86] PCT No.: PCT/US92/08780
§ 371 Date: Apr. 22, 1994
§ 102(e) Date: Apr. 22, 1994

[87] PCT Pub. No.: WO93/07869
PCT Pub. Date: Apr. 29, 1993

[30] Foreign Application Priority Data

Oct. 25, 1991 [GB] United Kingdom ................. 9122735

[51] Int. Cl.$^6$ .................. A61K 31/405; A61K 31/44; A61K 31/55
[52] U.S. Cl. .................... 514/409; 514/212; 514/278
[58] Field of Search ......... 514/409, 212, 278

[56] References Cited

U.S. PATENT DOCUMENTS 4,963,557 10/1990 Badger et al. ...................... 514/278

Primary Examiner—Raymond J. Henley, III
Assistant Examiner—William R. A. Jarvis
Attorney, Agent, or Firm—Wayne J. Dustman; Stephen Venetianer; Edward T. Lentz

[57] ABSTRACT

This invention discloses a method of treating hyperlipidemia in a mammal by administering an effective amount of a substituted azaspirane.

13 Claims, No Drawings

METHODS OF TREATING HYPERLIPIDEMIA WITH SUBSTITUTED AZASPIRANES

This invention relates to a method of treatment of hyperlipidemia in a mammal, including a human, in need thereof which comprises administering to such mammal an effective therefor amount of a substituted azaspirane.

BACKGROUND OF THE INVENTION

Badger et al., U.S. Pat. No. 4,963,557 (Badger I) discloses compounds of the formula

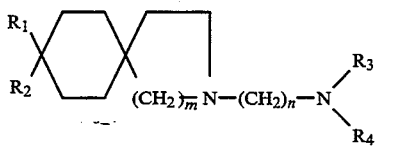

wherein: n is 3–7; m is 1 or 2; $R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms; $R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

Badger I does not disclose or claim the compounds of Formula I as antihyperlipidemic agents.

SUMMARY OF THE INVENTION

This invention relates to a a method of treatment of hyperlipidemia in a mammal, including a human, in need thereof which comprises administering to such mammal an effective therefor amount of a compound of the formula

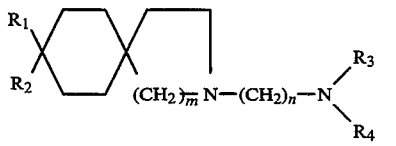

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;
$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms;
or a pharmaceutically acceptable salt or hydrate or solvate thereof.

DETAILED DESCRIPTION OF THE INVENTION

The term "hyperlipidemia" as used in the specification and in the claims is meant the presence of an abnormally high level of lipids in the blood.

The term "antihyperlipidemic" as used herein is meant the lowering of excessive lipid concentrations to desired levels.

Preferred lipids, of which high levels thereof are treated by the presently invented methods, are; cholesterol, triglycerides and low-density lipoproteins.

The preparation of all compounds of Formula (I) and pharmaceutically acceptable salts, hydrates and solvates and formulations thereof is discolsed in U.S. Pat. No. 4,963,557, the entire disclosure of which is hereby incorporated by reference.

As used herein, the term "compound A" refers to the dihydrochloride salt of a compound of Formula (I) where $R^1$ and $R^2$ are propyl, $R^3$ and $R^4$ are methyl, m is 1 and n is 3 which is N,N-dimethyl-8,8-dipropyl-2-azaspiro[4,5]decane-2-propanamine dihydrochloride.

It has now been discovered that compounds of Formula (I) and pharmaceutically acceptable salts or hydrates or solvates thereof are useful for treatment of hyperlipidemia in a mammal, including humans, in need of such treatment.

Compound A was tested for its in vivo potency in lowering serum cholesterol in normal cholesterolemic dogs in two experiments. To perform experiment I a total of 6 pure bred normal cholesterolemic beagle dogs, 3 male and 3 female (Marshall Animal Farms, Inc., North Rose, N.Y.) were used. The dogs weighed between 10 and 15 kilograms at the start of the study. The dogs were maintained on tap water, which was available ad libitum from an automatic watering system, and standard laboratory chow (Pruina Laboratory Cainine Chow ®). The 6 dogs were set up in 6 units as follows:

| Unit 1 | Male control, dosed orally once a day with vehicle alone. |
| Unit 2 | Male low dose, dosed orally once a day with 3.0 mg/kg of compound A. |
| Unit 3 | Male high dose, dosed orally once a day with 6.0 mg/kg of compound A. |
| Unit 4 | Female control, dosed orally once a day with vehicle alone. |
| Unit 5 | Female low dose, dosed orally once a day with 3.0 mg/kg of compound A. |
| Unit 6 | Female high dose, dosed orally once a day with 6.0 mg/kg of compound A. |

The cholesterol level of each dog was established 19 days before dosing, dosing began on day 1 and continued until day 29. The dogs were fed approximately 300 grams of the canine chow at least 1–2 hours before dosing. The dogs were fasted for approximately 16–20 hours prior to obtaining blood samples.

Experiment II was performed under the same procedure as experiment I. In experiment II 6 male pure bred normal cholesterolemic beagle dogs were set up in 2 groups as follows:

| Group 1 | Control, dosed orally once a day with vehicle alone. |
| Group 2 | Low dose, dosed orally once a day |

-continued with 1.0 mg/kg of compound A.

Dosing began on day 1 and continued until day 29. The cholesterol level of each dog was established on day 1, prior to dosing.

The test compound was administered in a gelatin capsule and control dogs received in an empty capsule. Serum cholesterol levels in the blood samples were determined on a Hitachi 705 chemistry analyzer employing Boehringer Mannheim Diagnostics commercial reagents.

The dogs treated with compound A realized a significant decrease in serum cholesterol levels. Thus, the administration of a compound of Formula I results in a therapeutic lowering of serum cholesterol levels in mammals.

The method of this invention of treating hyperlipidemia comprises administering to a mammal, including humans, in need thereof an effective therefor amount of a compound of Formula I.

An effective antihyperlipidemic amount of a compound of Formula (I) or a pharmaceutically acceptable salt or hydrate or solvate thereof (i.e. active ingredient) is useful in treating, prophylactically or therapeutically, any disease state in a mammal, including a human, which is exacerbated or caused by excessive lipid levels. Preferably, the disease state is selected from hyperlipidemic syndromes, atherosclerosis and transplant arteriolosclerosis. Particularly preferred is the disease state of atherosclerosis.

This invention relates to a method of treatment of hyperlipidemia in a mammal, including a human, in need thereof which comprises administering an effective therefor amount of a compound of Formula (I) or a pharmaceutically acceptable salt or hydrate or solvate thereof. A compound of Formula (I) or a pharmaceutically acceptable salt or hydrate or solvate thereof can be administered to such mammal, including a human, in a conventional dosage form prepared by combining a compound of Formula (I) or a pharmaceutically acceptable salt or hydrate or solvate thereof, with a conventional pharmaceutically acceptable carrier or diluent according to known techniques, such as those described in Badger (I), U.S. Pat. No. 4,963,557.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to a mammal, including a human, in need of antihyperlipidemic activity in an amount sufficient to lower lipid concentration to desired levels.

The route of administration of the Formula (I) compound is not critical but is usually oral or parenteral, preferably oral. The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from about 0.1 mg/kg to about 1 mg/kg. The daily oral dosage regimen will preferably be from about 0.01 mg/kg to about 10 mg/kg of total body weight.

Preferably, each parenteral dosage unit will contain the active ingredient in an amount of from about 0.1 mg to about 100 mg. Preferably each oral dosage unit will contain the active ingredient in an amount of from about 0.1 mg to about 100 mg.

The compounds of Formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

While it is possible for an active ingredient to be administered alone, it is preferable to present it as a pharmaceutical formulation.

It will be recognized by one of skill in the art that the optimal quantity and spacing of individual dosages of a compound of formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day and duration of therapy, can be ascertained by those skilled in the art using conventional course of treatment determination tests.

Following are the results of testing the compounds of this invention.

TABLE I

The effect of N,N-dimethyl-8,8-dipropyl-2-azaspiro[4,5]decane-2-propanamine dihydrochloride (Compound A) on lowering serum cholesterol levels in normal cholesterolemic dogs from experiment I.

TABLE I

| Unit No. N = 1/unit | Treatment | Cholesterol Level (mg/dl) at Identical days of Treatment | | | |
|---|---|---|---|---|---|
| | | −19 | 4 | 15 | 29 |
| Unit 1 | None Male Control | 148 | 144 | 144 | 138 |
| Unit 2 | Male 3.0 mg/kg of Compound A | 140 | 151 | 105 | 81 |
| Unit 3 | Male | 135 | 114 | 57 | 31 |

TABLE I-continued

| Unit No. N = 1/unit | Treatment | Cholesterol Level (mg/(dl) at Identical days of Treatment | | | |
|---|---|---|---|---|---|
| | | −19 | 4 | 15 | 29 |
| Unit 4 | 6.0 mg/kg of Compound A None Female Control | 179 | 178 | 168 | 170 |
| Unit 5 | Female 3.0 mg/kg of Compound A | 130 | 100 | 71 | 40 |
| Unit 6 | Female 6.0 mg/kg of Compound A | 138 | 108 | 63 | 54 |

The data in the above table demonstrates the therapeutic effect of compounds of Formula I on serum cholesterol levels.

TABLE II

The effect of N,N-dimethyl-8,8-dipropyl-2-azaspiro[4,5]decane-2-propanamine dihydrochloride (Compound A) on lowering serum cholesterol levels in normal cholesterolemic dogs from experiment II.

TABLE II

| Group No. n = 3/group | Treatment | Cholesterol Level (Group Mean ± SEM mg/dl) at Identical days of Treatment | | |
|---|---|---|---|---|
| | | Day 1 | Day 15 | Day 29 |
| Group 1 | Vehicle | 137.7 ± 10.5 | 129.7 ± 7.2 | 136.3 ± 10.3 |
| Group 2 | 1.0 mg/kg of Compound A | 161.0 ± 15.5 | 97.7 ± 6.2 | 74.7 ± 4.8 |

The data in the above table demonstrates the therapeutic effect of compounds of Formula I on serum cholesterol levels.

In addition, the compounds of the present invention can be co-administered with further active ingredients, such as other compounds known for the treatment of elevated lipid levels such as acyl-CoA: Cholesterol acyltransferase (ACAT) inhibitors, HMGCoA reductase inhibitors and bile acid sequestrants.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1—CAPSULE COMPOSITION

An oral dosage form for administering Formula (I) compounds is produced by filing a standard two piece hard gelatin capsule with the ingredients in the proportions shown in Table III, below.

TABLE III

| INGREDIENTS | AMOUNTS |
|---|---|
| N,N-dimethyl-8,8-dipropyl-2-azaspiro[4,5]decane-2-propanamine dihydrochloride | 25 mg |
| Lactose | 55 mg |
| Talc | 16 mg |
| Magnesium Stearate | 4 mg |

EXAMPLE 2—INJECTABLE PARENTERAL COMPOSITION

An injectable form for administering Formula (I) compounds is produced by stirring 1.5% by weight of N,N-dimethyl-8,8-dipropyl-2-azaspiro[4,5]decane-2-propanamine dihydrochloride in 10% by volume propylene glycol in water.

EXAMPLE 3—TABLET COMPOSITION

The sucrose, calcium sulfate dihydrate and Formula (I) compound shown in Table IV below, are mixed and granulated in the proportions shown with a 10% gelatin solution. The wet granules are screened, dried, mixed with the starch, talc and stearic acid, screened and compressed into a tablet.

TABLE IV

| Ingredients | Amounts |
|---|---|
| N,N-dimethyl-8,8-dipropyl-2-azaspiro[4,5]decane-2-propanamine dihydrochloride | 20 mg |
| calcium sulfate dehydrate | 30 mg |
| sucrose | 4 mg |
| starch | 2 mg |
| talc | 1 mg |
| stearic acid | 0.5 mg |

While the above descriptions and examples fully describe the invention and the preferred embodiments thereof, it is understood that the invention is not limited to the particular disclosed embodiments coming within the scope of the following claims.

What is claimed is:

1. A method of treating hyperlipidemia in a mammal comprising administering to said mammal a therapeutically effective amount of a compound of the formula

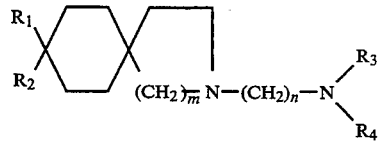

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;
$R^3$ and $R^4$ are the same or different and are selected from hydrogen or straight chain alkyl having 1–3 carbon atoms; or $R^3$ and $R^4$ are joined together with the nitrogen to form a heterocyclic group having 5–8 atoms;
or a pharmaceutically acceptable salt or hydrate or solvate thereof.

2. The method of claim 1 wherein the compound is N,N-dimethyl-8,8-dipropyl-2-azaspiro[4,5]decane-2-propanamine; or a pharmaceutically acceptable salt, hydrate or solvate thereof.

3. The method of claim 1 wherein the mammal is afflicted with hyperlipidemic syndrome.

4. The method of claim 1 wherein the mammal is afflicted with atherosclerosis.

5. The method of claim 1 wherein the mammal is afflicted with transplant arteriolosclerosis.

6. The method of claim 1 wherein the mammal is in need of lower cholesterol and triglyceride levels.

7. The method of claim 1 wherein the mammal is in need of lower cholesterol levels.

8. The method of claim 1 wherein the mammal is in need of lower triglyceride levels.

9. The method of claim 1 wherein the mammal is in need of lower low-density lipoprotein levels.

10. The method of claim 1 wherein the compound is administered orally.

11. The method of claim 10 wherein from about 0.01 mg/kg to about 10 mg/kg of compound is administered per day.

12. The method of claim 1 wherein the compound is administered parenterally.

13. The method of claim 12 wherein from about 0.01 mg/kg to about 10 mg/kg of compound is administered per day.

* * * * *